United States Patent [19]
Euteneuer et al.

[11] Patent Number: 5,567,203
[45] Date of Patent: Oct. 22, 1996

[54] BALLOON DILATATION CATHETER WITH PROXIMAL HYPOTUBE

[75] Inventors: Charles L. Euteneuer, St. Michael; Richard C. Mattison, Corcoran; Daniel O. Adams, Blaine; Thomas R. Hektner, Minnetonka; Peter T. Keith, Edina, all of Minn.

[73] Assignee: SCIMED Life Systems, Inc., Maple Grove, Minn.

[21] Appl. No.: 473,477

[22] Filed: Jun. 7, 1995

Related U.S. Application Data

[63] Continuation of Ser. No. 782,242, Oct. 23, 1991, which is a continuation of Ser. No. 433,711, Nov. 13, 1989, abandoned, which is a continuation-in-part of Ser. No. 162,004, Feb. 29, 1988, Pat. No. 4,943,278.

[51] Int. Cl.$^6$ ................................................ A61M 29/00
[52] U.S. Cl. ................................................ 604/96; 606/194
[58] Field of Search ........................ 604/96–103, 282; 606/192–196; 600/18, 115, 116; 128/207.15

[56] References Cited

U.S. PATENT DOCUMENTS

| | | |
|---|---|---|
| Re. 33,166 | 2/1990 | Samson . |
| 4,276,874 | 7/1981 | Wolvek et al. . |
| 4,573,470 | 3/1986 | Samson et al. . |
| 4,641,654 | 2/1987 | Samson et al. . |
| 4,655,746 | 4/1987 | Daniels et al. . |
| 4,664,113 | 5/1987 | Frisbie et al. . |
| 4,748,982 | 6/1988 | Horzewski et al. . |
| 4,762,129 | 8/1988 | Bonzel . |
| 4,771,777 | 9/1988 | Horzewski et al. . |
| 4,821,722 | 4/1989 | Miller et al. . |
| 4,824,435 | 4/1989 | Giesy et al. . |
| 4,838,268 | 6/1989 | Keith et al. . |
| 4,846,174 | 7/1989 | Willard et al. . |
| 4,848,344 | 7/1989 | Sos et al. . |
| 4,875,481 | 10/1989 | Higgins et al. . |
| 4,877,031 | 10/1989 | Conway et al. . |
| 4,892,519 | 1/1990 | Songer et al. . |
| 4,896,670 | 1/1990 | Crittenden . |
| 4,906,241 | 3/1990 | Noddin et al. . |
| 4,917,088 | 4/1990 | Crittenden . |
| 4,976,720 | 12/1990 | Machold et al. . |
| 4,988,356 | 1/1991 | Crittenden et al. . |
| 4,998,917 | 3/1991 | Gaiser et al. . |
| 4,998,923 | 3/1991 | Samson et al. . |
| 5,003,989 | 4/1991 | Taylor et al. . |
| 5,034,001 | 7/1991 | Garrison et al. . |
| 5,040,548 | 8/1991 | Yock . |
| 5,050,606 | 9/1991 | Tremulis . |
| 5,061,273 | 10/1991 | Yock . |
| 5,102,390 | 4/1992 | Crittenden et al. . |
| 5,104,376 | 4/1992 | Crittenden . |
| 5,147,377 | 9/1992 | Sahota . |
| 5,171,222 | 12/1992 | Euteneuer et al. . |
| 5,180,367 | 1/1993 | Kontos et al. . |
| 5,180,368 | 1/1993 | Garrison . |
| 5,232,445 | 8/1993 | Bonzel . |
| 5,242,394 | 9/1993 | Tremulis . |
| 5,279,560 | 1/1994 | Morrill et al. . |
| 5,318,529 | 6/1994 | Kontos . |

*Primary Examiner*—Corrine M. McDermott
*Attorney, Agent, or Firm*—Robert E. Atkinson

[57] ABSTRACT

An intravascular balloon catheter is disclosed which includes a proximal hypotube shaft segment, a distal polymer shaft segment, a distally-mounted inflatable balloon segment, and a hollow tubular member having a proximal end connected to the distal end of the hypotube shaft segment such that the lumen of the hollow tubular member is in communication with the exterior of the balloon catheter and the distal end of the hollow tubular member is connected to the distal end of the balloon.

30 Claims, 3 Drawing Sheets

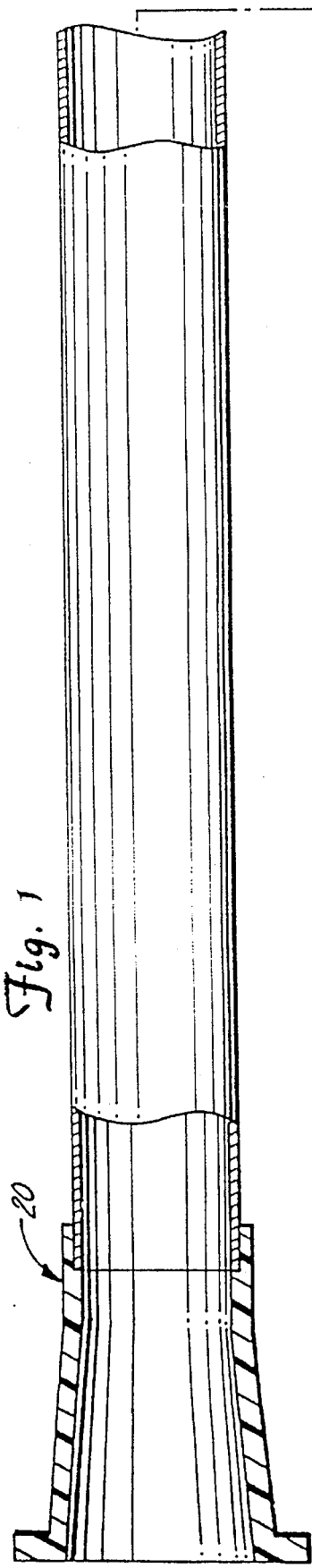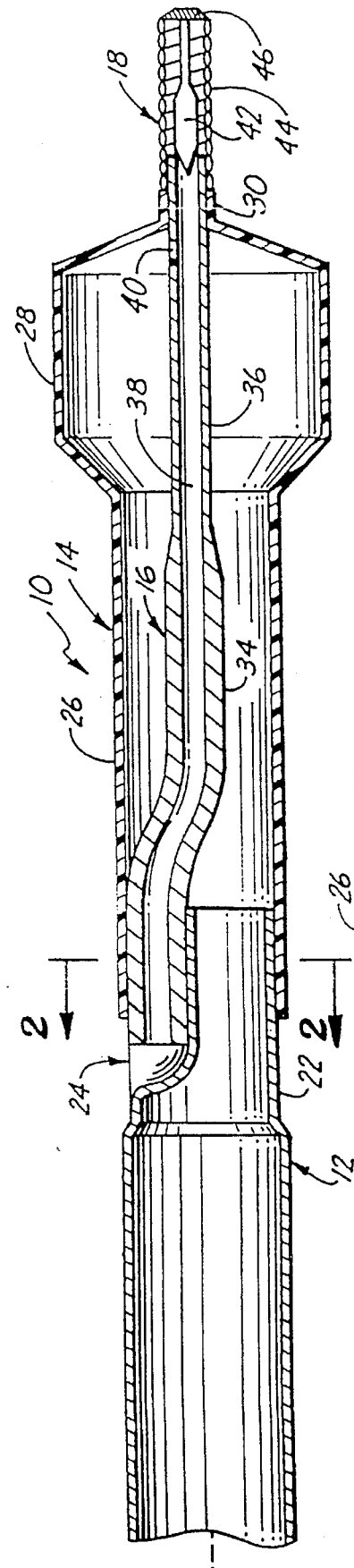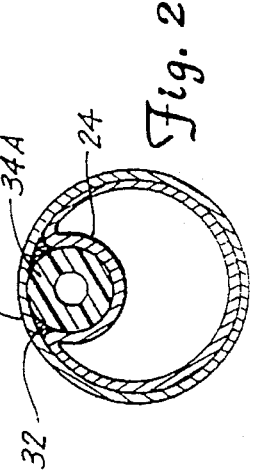

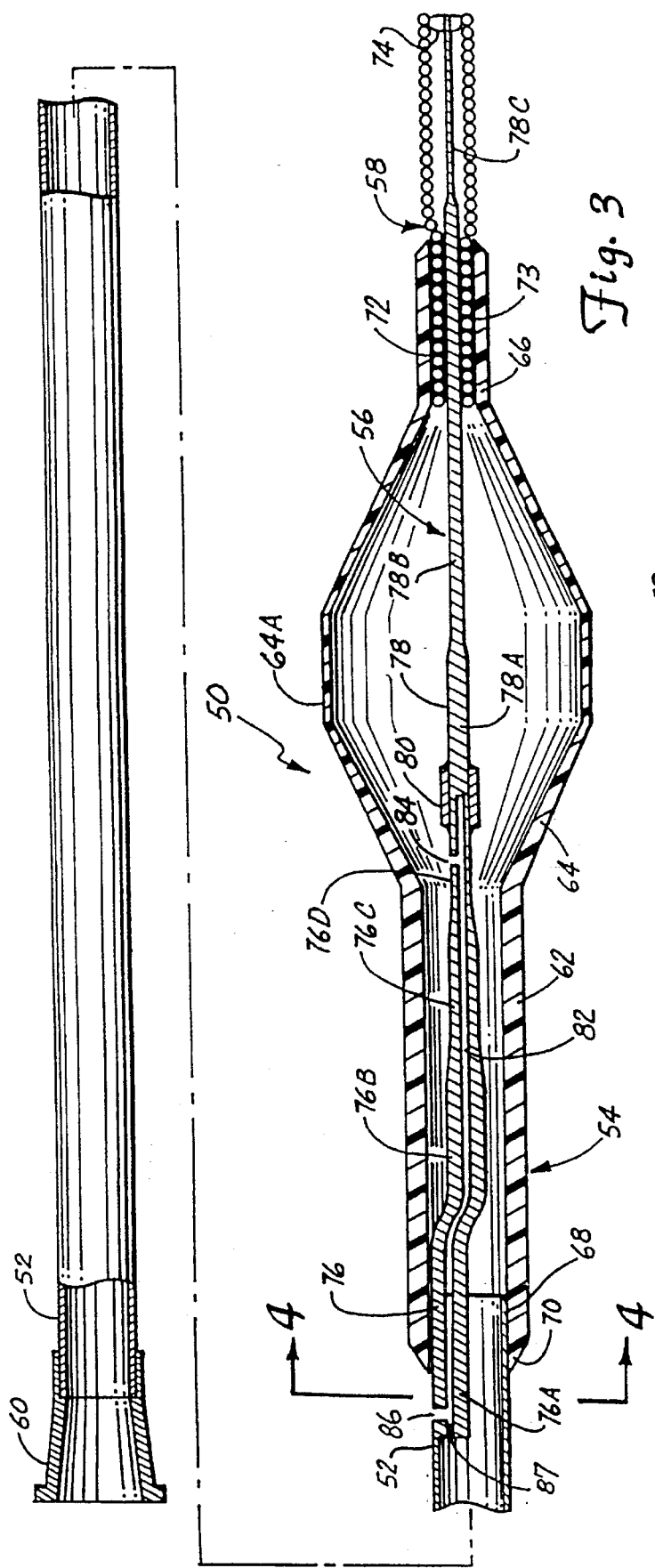

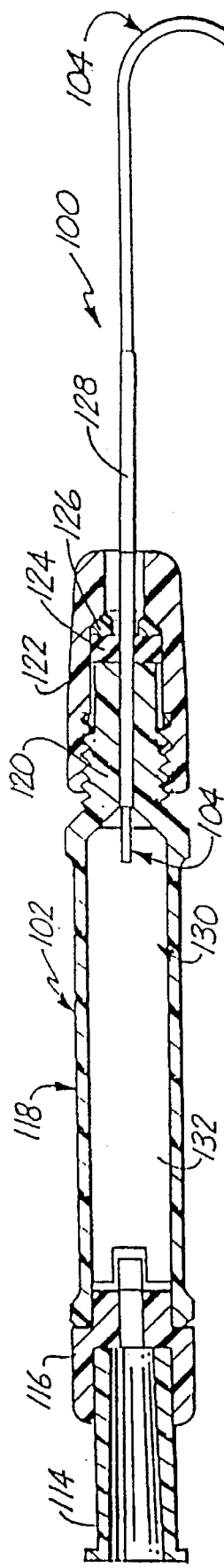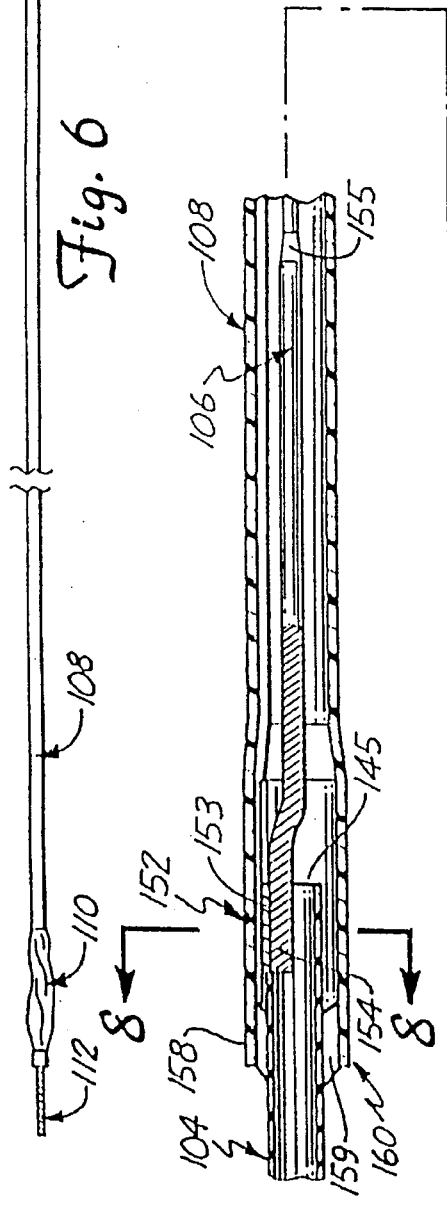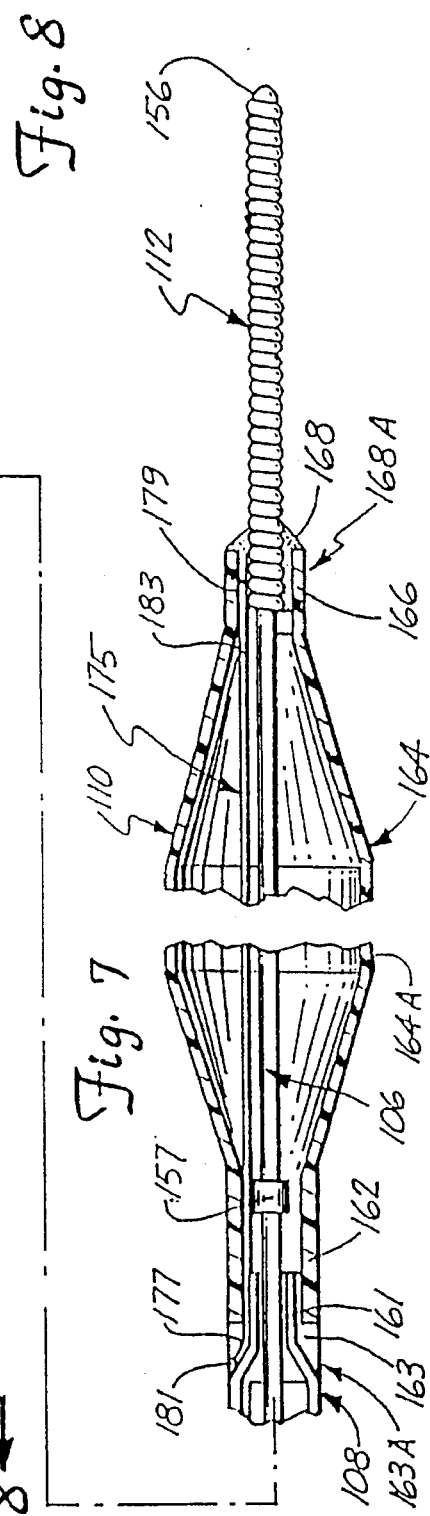

5,567,203

BALLOON DILATATION CATHETER WITH PROXIMAL HYPOTUBE

This is a continuation of application Ser. No. 07/782,242, filed on Oct. 23, 1991, pending which is a continuation of application Ser. No. 07/433,711, filed on Nov. 13, 1989, now abandoned, which is a continuation-in-part of application Ser. No. 07/162,004, filed on Feb. 29, 1988, now U.S. Pat. No. 4,943,278, issued on Jul. 24, 1990.

BACKGROUND OF THE INVENTION

The present invention relates to the field of angioplasty. In particular, the present invention relates to a dilatation balloon catheter.

Angioplasty has gained wide acceptance in recent years as an efficient and effective method for treating types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying fluid under pressure through an inflation lumen to the balloon. The inflation of the balloon causes stretching of the artery and pressing of the lesion into the artery wall to reestablish acceptable blood flow through the artery.

In order to treat very tight stenoses with small openings, there has been a continuing effort to reduce the profile of the catheter so that the catheter cannot only reach but also cross such a very tight stenosis.

In addition, a percutaneous transluminal coronary angioplasty (PTCA) system has been developed by applicant's assignee which makes use of a very low profile balloon catheter or "dilating guide wire" over which a second dilatation catheter can pass. The smaller dilating guide wire is first moved across a very tight stenosis, and the balloon of the dilating guide wire is inflated to partially open the stenosis. Subsequently, the larger diameter dilatation catheter is advanced over the dilating guide wire and across the stenosis. The balloon of the larger diameter catheter is then inflated to open further the stenosis.

The need to decrease dilatation catheter profiles has, however, brought with it certain practical limitations. In particular, the ability to transmit torque from the proximal to the distal end of the guide wire (or the catheter) in order to steer its distal tip through the vascular system and across a stenosis has been compromised. The need to reduce profile can compromise purgeability using conventional vacuum techniques. Therefore, there is a continuing need for improved torque response and tip control along with continued efforts for reduction in catheter profile, while facilitating a positive pressure purge.

SUMMARY OF THE INVENTION

A first embodiment of the present invention is an intravascular balloon catheter comprising a balloon having a proximal waist segment, an inflatable segment and a distal waist segment. A metallic tube is connected to the proximal waist segment and a hollow core member is connected at its distal end to the distal waist segment. The proximal end of the hollow core member is connected to the distal end of the metallic tube such that the lumen of the hollow core member is in communication with the exterior of the balloon catheter. The distal end of the metallic tube may have a diminishing profile or a taper. The distal end of the metallic tube may also be crimped. The hollow core member may extend through the interior of the proximal waist segment, the inflatable balloon segment, or the distal waist segment. The proximal waist segment and the inflatable segment may be integrally formed.

Another embodiment of the present invention is an intravascular balloon catheter having a hypotube proximal shaft portion. A tubular member is provided which has a proximal end connected to the distal end of the hypotube such that the lumen of the tubular member is in communication with the exterior of the balloon catheter. The distal end of the tubular member is connected to the distal end of an inflatable balloon. The distal end of the hypotube may have a diminishing profile or taper. The distal end of the hypotube may also be crimped. The tubular member may extend through the interior of the balloon.

Yet another embodiment of the present invention is an intravascular balloon catheter having an inflatable balloon, a metallic tube, and proximal waist connected therebetween. A hollow tubular member is provided which has a proximal end connected to the distal end of the metallic tube such that the lumen of the hollow tubular member is in communication with the exterior of the balloon catheter. The distal end of the hollow tubular member is connected to the distal end of the balloon. The distal end of the metallic tube may have a diminishing profile or taper. The distal end of the metallic tube may also be crimped. The hollow tubular member may extend through the interior of the proximal waist or the inflatable balloon. The proximal waist and the balloon may be integrally formed.

A further embodiment of the present invention is an intravascular balloon catheter having an elongate shaft with a proximal portion made of metal and a distal portion mad of a polymer. An inflatable balloon is connected to the distal portion of the elongate shaft. A hollow tubular member is connected to the elongate shaft such that the lumen of the hollow tubular member is in communication with the exterior of the balloon catheter. The hollow tubular member may also be connected to the inflatable balloon. The proximal metallic portion of the elongate shaft may have a distal end which has a diminishing profile. The proximal metallic portion of the elongate shaft may have a distal end which is crimped. The hollow tubular member may extend at least partially through the interior of the balloon.

BRIEF DESCRIPTION OF THE DRAWINGS

FIG. 1 is a sectional view of a first preferred embodiment of the balloon catheter of the present invention.

FIG. 2 is a sectional view along section 2—2 of FIG. 1.

FIG. 3 is a sectional view of a second preferred embodiment of the balloon catheter of the present invention.

FIG. 4 is a sectional view along section 4—4 of FIG. 3.

FIG. 5 is a detail view showing a brazed bond between the tube and core shown in FIG. 4.

FIG. 6 is a sectional view of a third preferred embodiment of the balloon catheter of the present invention.

FIG. 7 is an enlarged sectional view of a distal portion of the third preferred embodiment.

FIG. 8 is a sectional view along section 8—8 of FIG. 7.

DETAILED DESCRIPTION OF THE PREFERRED EMBODIMENTS

Catheter 10 shown in FIGS. 1 and 2 is a dilatation balloon catheter which includes main catheter tube or shaft 12, balloon member 14, core member 16, and spring tip 18.

Tube 12 is an elongated flexible thin walled metal tube, preferably of stainless steel or of stainless steel with a low friction coating such as polytetrafluoroethylene. Luer fitting 20 is mounted at the proximal end of tube 12 for connection to an inflation device (not shown) which provides fluid under pressure through the interior lumen of tube 12 for balloon inflation.

At its distal end, tube 12 has a section 22 of reduced outside diameter and a formed recess 24 in which the proximal end of core member 16 is attached, preferably by brazing.

Balloon member 14, which is preferably a polymer material such as a polyolefin, has a proximal or waist segment 26, a distensible balloon segment 28, and a small diameter distal segment 30. Proximal segment 26 is bonded to the distal end of tube 12 and to core member 16. An adhesive and sealing material 32 (such as an epoxy) is provided to seal together tube 12 and core member 16 with the proximal segment 26 of balloon member 14.

In the embodiment shown in FIGS. 1 and 2, core member 16 is generally aligned parallel with tube 12 and balloon member 14 and is coaxially aligned except for its proximal end. Core member 16 has a proximal section 34 of larger outer diameter and a distal section 36 of smaller outer diameter. Central vent passage 38 extends essentially the entire length of core member 16, and opens to the exterior of catheter 10 at the proximal end of core member 16. Vent opening 40 provides communication between vent passage 38 and the interior of balloon member 14 to allow for the positive pressure purging of air out through vent opening 40, vent passage 38, and the open proximal end of core member 16.

Distal segment 30 of balloon member 14 is bonded (such as by an epoxy) to the distal end of core segment 36, such as by brazing or soldering. In FIG. 1, core segment 36 extends out slightly beyond the end of distal segment 30, and spring tip 18 is attached to core segment 36. Spring tip 18 includes a solid core segment 42 (which blocks the distal end of vent passage 38), coiled spring 44, and brazed safety button 46. The more proximally located portions of spring 44 are preferably bonded or otherwise attached to the outer end of distal core segment 36.

Distensible segment 28 of balloon member 14 has (by special shaping, wall thickness, or material treatment) a greater tendency to expand under fluid pressure than waist segment 26. The inflation and deflation of balloon member 14, therefore, is primarily confined to distensible segment 28.

In FIG. 1, catheter 10 is shown in a condition in which distensible balloon segment 28 is inflated. Before being inserted into the patient, catheter 10 is connected to an inflation device (not shown) and liquid is supplied under pressure through the interior of tube 12 to the interior of balloon member 14. This liquid purges air contained within the interior of catheter 10 out through vent opening 40 and vent passage 38 to the exterior of catheter 10. Vent opening 40 and passage 38 are sized so that fluid pressure can be supplied to inflate balloon segment 28 without significant leaking of the inflation liquid, and so that air and a small plug of liquid will enter passage 38. When the air has been purged from the interior of catheter 10, the inflation device is then used to draw the liquid back so as to collapse balloon segment 28 around core member 16. This provides a low profile while catheter 10 is being inserted into the patient. The plug of liquid within vent passage 38, however, blocks air from re-entering the interior of balloon segment 28.

The advance of the contrast liquid into passage 38 is controlled by two factors. First, the liquid column is forced through the vent opening 40 by pressure applied to the liquid, and liquid flow is resisted to an extent by the small diameter (about 0.001 to about 0.003 inch) of vent opening 40. Second, once the liquid has entered the passage 38, capillary action which is governed by the surface tension between the liquid and the surface characteristics and diameter of passage 38 will allow the liquid into the core along a certain length until a state of equilibrium is reached. At this point, more pressure would be required to begin movement of the liquid in the column than catheter 10 can be subject to, and therefore the liquid advances no further. This applies to both the application of positive pressure and vacuum. For this reason, catheter 10 is not only ventable through vent opening 40 and passage 38, but is also self-sealing. No additional seal or valve is required to prevent liquid and pressure from bleeding off through this vent passage. The flow characteristics of the radiopaque liquid in the core are dependent on optimization of the capillary action and static breakaway pressure shears.

Catheter 10 is then inserted into the patient and its distal end is advanced through the patient's vascular system to the location of the stenosis which is to be treated. A significant advantage of the present invention is the improved "steerability", "pushability" and "torqueability" (i.e., torque transfer) characteristics which are provided by tube 12. Unlike prior art low profile balloon catheters, in which the main catheter tube or shaft is made of a flexible plastic material, the thin walled metal tube 12 used in catheter 10 of the present invention provides sufficient flexibility to traverse bends, while having improved pushability and improved torque transmitting characteristics.

FIGS. 3 and 4 show dilatation catheter 50, which is another embodiment of the present invention. Catheter 50 includes metal tube 52, balloon member 54, core member 56, spring tip 58 and luer fitting 60.

Tube 52 is an elongated flexible thin walled metal tube of a material such as 304 stainless steel. Tube 52 preferably has a low coefficient of friction coating, such as polytetrafluoroethylene. In one preferred embodiment of the present invention, metal tube 52 has a length of about 43 inches, an inside diameter of about 0.020 inch and an outside diameter of about 0.024 inch.

At the proximal end of metal tube 52 is luer fitting 60. An inflation device (not shown) is connected to fitting 60 for balloon inflation/deflation.

Balloon member 54 is mounted at the distal end of metal tube 52, and is preferably an axially stretchable thermoplastic balloon material which has the ability to have small inside diameter and outside diameter dimensions and a thin wall, while still maintaining an acceptably high burst rating (for example, ten to twelve atmospheres) and a compliance comparable to other balloons used in angioplasty dilatation catheters. Balloon member 54 has a proximal or waist segment 62, a distensible balloon segment 64 and a distal segment 66. Balloon segment 64 is shown in FIG. 3 in its fully inflated condition.

In a preferred embodiment of the present invention, proximal waist segment 62 has a length of about 12 inches, an outside diameter of about 0.034 inch and a wall thickness of about 0.0045 inch. The proximal end of waist segment 62 overlaps and is bonded by epoxy bond 68 to the distal end of metal tube 52 and to a portion of core member 56. Proximal end 70 of waist segment 62 is beveled to provide a smooth profile as catheter 50 is withdrawn from the patient.

As shown in FIG. 3, the wall thickness of balloon segment 64 has a wall thickness which varies from about 0.0045 inch at the end which joins waist segment 62, to a minimum thickness of about 0.001 to about 0.003 inch in central section 64A, (depending on balloon outside diameter) to a wall thickness of about 0.004 inch at the end which joins to distal segment 66. Central segment 64A is about 0.8 inch in length.

Distal segment 66 is bonded by an epoxy bond 72 to spring tip coil 58, which in turn is attached by braze joint 73 to core member 56. The outside diameter of distal segment 66 is about 0.022 inch and the inside diameter is about 0.014 inch. In the bonding region, spring tip coil 58 has an outside diameter of about 0.011 inch to about 0.012 inch, and has a similar or slightly larger outside diameter distal to the bonding region. The diameter of the coil wire forming spring tip coil 58 is about 0.003 inch.

Spring tip coil 58 extends about 0.8 inch beyond the distal segment 66, and is connected to the distal end of core 56 by a braze bond or safety button 74.

The position of the epoxy bond 72 at the same location as braze joint 73 minimizes the length of the relatively stiff region formed by these two joints.

Since the objective of catheter 50 is the ability to conform to rather tortuous passages, minimizing the lengths of the stiff region near the distal end of catheter 50 is an advantageous feature of the present invention.

In the embodiment shown in FIG. 3, core member 56 includes vent tube core 76 and solid distal core 78, which are connected together in end-to-end fashion by braze joint and marker 80.

Vent tube core 76 has four sections 76A–76D of differing outside diameters. In a preferred embodiment, segment 76A has an outside diameter of about 0.012 inch, segment 76B has an outside diameter of about 0.009 inch, segment 76C has an outside diameter of about 0.007 inch, and segment 76D has an outside diameter of about 0.006 inch. This transition of decreasing outside diameter in the direction toward the distal end takes advantage of typical curvature of anatomy that catheter 50 will experience in the human body. Preferably, segment 76B has a length of about 4.5 inches and is flexible enough to pass through the aortic arch when the balloon segment 64 is trying to cross the lesion. Segment 76C of vent tube core 76 is preferably about 6 inches in length and is more flexible in order to negotiate the coronary arteries which are typically more tortuous than the aortic arch.

Extending through vent tube core 76 is vent passageway 82, which opens to the interior of balloon segment 64 near the proximal end through vent opening 84 and opens to the exterior of catheter 50 through opening 86. Plug 87 blocks the proximal end of vent passage 82 so that pressurized fluid from the interior of metal tube 52 cannot directly enter the proximal end passage 82 and flow out through opening 86.

As shown in FIGS. 3–5, segment 76A of vent tube core 76 is positioned in slot 88 which is formed in the distal end of metal tube 52. In a preferred embodiment, slot 88 is about 0.011 inch wide (which is slightly narrower than the outside diameter of segment 76A) and is about 0.025 inch long. Slot 88 is preferably formed by electrodischarge machining, and segment 76A is brazed in position in slot 88 so that a seal is formed between segment 76A and tube 52.

This preferred bonding of vent tube core 76 to metal tube 52 has the advantage that tube 52 and core 76 maintain good straightness with respect to one other (which is critical for torqueability requirements to prevent whipping of the distal end of catheter 52 as torque is applied to tube 52). In addition, the flow lumen is not as restricted as it would be without the presence of slot 88. In addition, since both the surfaces of vent tube core 76 and metal tube 52 are exposed during processing, the weld can be more reliably made.

It should be noted that the drawings are not drawn to scale. In FIG. 3, for example, the transition of vent core tube 76 from an off-axis connection to tube 52 to a generally coaxial position in more distal portions is much more gradual than shown.

Solid distal core 78 has a segment 78A which has the same outside diameter (0.006 inch) as segment 76D, a segment 78B having an outside diameter of 0.004 inch, and a flat ribbon segment 78C within spring tip 58 which is about 0.001 inch thick and about 0.003 inch wide.

In a preferred embodiment of the present invention, vent tube core 76 and solid distal core 78 are made of the same material, which is preferably a high strength stainless steel or other high strength alloy. 17-7 PH stainless, 18-8 PH stainless or 400 Series heat treatable stainless steel are examples of such high strength materials. The high strength characteristics of vent tube core 76 and solid distal core 78 reduces the chances of them taking on a permanent set when forced through a typical tortuous human anatomy.

In another embodiment of the present invention which is generally similar to the embodiment shown in FIGS. 3–5, except that core member 56 is a single solid core member. In this case, the vent passageway shown in FIG. 3 is not used, and core member 56 can be formed from a single solid wire core and then machined to the desired dimensions.

The advantage of this alternative embodiment of FIG. 5 is that generally a solid wire has somewhat greater strength and hardness than a tube of the same outside diameter. In addition, because core member 56 is an integral member, a bond between two sections of the core member is not required. In order to purge this alternative embodiment catheter, a conventional vacuum purge can be used.

FIGS. 6, 7 and 8 show dilatation catheter 100, which is another embodiment of the present invention. Catheter 100 includes manifold 102, metal tube 104, core 106, waist tube 108, balloon member 110 and spring tip 112.

Manifold 102 has a luer fitting 114 at its proximal end, for connection to an inflation device (not shown) which provides fluid under pressure to catheter 100. Lure fitting 114 is connected to a first end cap 116, which in turn is connected to a manifold body 118. Manifold body 118 has a reduced distal end portion 120, onto which is threadably mounted a second end cap 122. Retained between second end cap 122 and distal end portion 120 are an annual compression sleeve 124 and a manifold washer 126. Distal end portion 120 of manifold body 118, sleeve 124, washer 126 and second end cap 122 all have central longitudinal openings therethrough for reception of a strain relief tube 128, as seen in FIG. 6. Received within strain relief tube 128, (which is preferably formed from a polyolefin copolymer material and adhered to tube 104) is a proximal end portion of metal tube 104, with that proximal end portion extending proximally through distal end portion 120 of manifold body 118 and into an internal cavity 130 in manifold body 118. One or more inserts 132 are also in cavity 130, to take up the space therein and reduce the need for inflation fluid in the catheter 100. First end cap 116 also has a central opening therethrough, to permit inflation fluid to flow between the luer fitting 114 and cavity 130.

In a preferred embodiment, luer fitting 114 and first end cap 116 are secured together by an adhesive material, as are first end cap 116 and manifold body 118. In addition, second end cap 122 is preferably secured by an adhesive to distal end portion 120 of manifold body 118, in addition to the threaded engagement thereof. Tightening of the second end cap 122 onto distal end portion 120 of manifold body 118 compresses sleeve 124 to create a seal about strain relief tube 128.

No adhesives are used to secure second end cap 122 and strain relief tube 128 to distal end portion 120 of manifold body 118 when selective removal of second end cap 122 from manifold body 118 is desired. Such removal also relieves the gripping force on tube 104 (through strain relief tube 128) and would permit disengagement of tube 104 and manifold 102. This in turn would allow certain catheter exchange techniques which are not possible with manifold 102 adhered to tube 104.

Tube 104 is an elongated flexible thin walled metal tube, preferably a stainless hypotube with a low friction coating such as polytetrafluoroethylene. In one preferred embodiment of the present invention, metal tube 104 has a length of about 44 inches, an inside diameter of about 0.017 inch, and an outside diameter of about 0.024 inch (1.8 French).

At a distal end 145, tube 104 has a longitudinal slot 150 formed therein. In a preferred embodiment, slot 150 is about 0.011 inch wide, is about 0.25 inch long.

Core 106 is an elongated member which is preferably formed from a high-strength stainless steel or other high-strength alloy, and which is connected to tube 104 at a first bonding region 152. 17-7 PH stainless, 18-8 PH stainless, and 300 or 400 series stainless steel are examples of such high-strength materials. The high strength characteristics of core 106 reduces the chances of it taking on a permanent set when forced through a typically tortuous human anatomy. A proximal end 154 of core 106 is received within slot 150 and brazed or soldered thereto to securely fasten core 106 to tube 104 to define first bonding region 152.

In the embodiment of the present invention illustrated in FIGS. 6, 7 and 8, core 106 is a single solid core wire, which is reduced in cross-section by elongated tapers or stepped reductions (e.g., taper 155) as it extends distally from tube 104. This reduction in cross-section further enhances the flexibility of core 106 as it extends distally, and through balloon 110.

This preferred bonding of core 106 to metal tube 104 has the advantage that tube 104 and core 106 maintain good straightness with respect to one another (which is critical for torqueability requirements in order to prevent whipping of the distal end of the catheter 100 as torque is applied to tube 104). As seen in FIG. 7, proximal end 154 of core 106 is offset from the axis of catheter 100, but assumes a central axial alignment distally of tube 104, as it extends through waist tube 108 and balloon 110. In this regard, it should again be noted that the drawings herein are not to scale. In FIG. 7, for example, the transition of core 106 from an off-axis connection (to tube 104) to a generally coaxial position distally therefrom is more gradual than shown.

As discussed above with reference to prior core designs, at its proximal end, core 106 may have an outside diameter of about 0.012 inch, reducing in size distally (for increased distal flexibility) until it is received within spring tip 112. In its very distal portions, core 106 may be formed as a thin, flat ribbon segment within spring tip 112, which is then secured to spring tip 112 at the distal end thereof by a welded safety button 156. Preferably, one or more radiopaque markers 157 are secured to core 106 and spring tip 112 is formed from radiopaque material (such as a platinum alloy) to aid in locating catheter 100 in the patient's vascular system by fluoroscopy.

Waist tube 108 is an elongated flexible tube, also mounted to tube 104 as seen in FIG. 7, and is preferably formed from a polymer material such a high density polyethylene (which is a relatively lubricious, flexible and high strength material). A proximal end 158 of waist tube 108 extends proximally over distal end 145 of tube 104. Proximal end 158 of waist tube 108 is secured concentrically about tube 104 by a suitable adhesive 159 (such as cyanoacrylate), at a second bonding region 160 proximally spaced from first bonding region 152 between tube 104 and core 106. Those distal portions of tube 104 in bondings regions 152 and 160 are not coated with lubricious material.

Waist tube 108 extends distally about core 106 from tube 104. At its proximal end 158, waist tube 108 has an outer diameter of about 0.031 inch, and tapers down to an outer diameter of about 0.026 inch distally therefrom. In this reduced distal section, the inner diameter of waist tube 108 is about 0.021 inch, and this reduced section is about 11.10 inches long. Preferably, the wall thickness of waist tube 108 is about 0.0025 inch. The reduction in diameters of waist tube 108 (and accordingly, catheter 100) allows better flexibility and "trackability" for catheter 100 in the patient's vascular system. By injecting radiopaque dyes therein, the patient's arterial lumens are made visible on a fluoroscope. Reducing the diameter of catheter 100 allows more dye to flow adjacent and around catheter 100, thus making the lumen areas more visible which further aids in the positioning of catheter 100 in the artery and evaluation of dilatation performance.

By mounting proximal end 158 of waist tube 108 to tube 104 proximally of first bonding region 152 between tube 104 and core 106, a smoother external surface transition is presented and made between components of catheter 100 adjacent distal end 145 of tube 104. Further, there are no material discontinuities or bumps adjacent first bonding region 152 external of catheter 100. This arrangement also provides a more uniform bond structure (annular with no obstructions) for securing waist tube 108 to tube 104 than might otherwise be possible (see, e.g., FIG. 8).

At its distal end 161, waist tube 108 is connected to a proximal balloon segment or waist 162 of balloon 110, using a suitable adhesive and sealing material 163 (such as an epoxy) thereby defining a third bonding region 163A. As in the prior described embodiments, balloon 110 is preferably formed from an axially-stretchable thermoplastic balloon material which has the ability to have small inside diameter and outside diameter dimensions, and a thin wall, while still maintaining an acceptably high burst rating (for example, 10 to 12 atmospheres) and a compliance comparable to other balloons used in angioplasty dilatation catheters. Preferably, this balloon material is formed from a polymer material such as polyolefin copolymer.

Balloon 110 has a distensible balloon segment 164 (shown in FIG. 7 in its fully inflated condition) and a distal balloon segment or waist 166. In a preferred embodiment of the present invention, proximal waist 162 has a length of about 0.50 inch, an outer diameter of about 0.031 inch and a wall thickness of about 0.005 inch. The wall thickness of distensible balloon segment 164 varies from about 0.005 inch at the end which joins waist 162, to a minimum thickness of about 0.0018 inch to about 0.0025 inch in central section 164A (depending upon balloon outside diameter) to a wall thickness of about 0.005 inch at the end which joins to distal waist 166. Central segment 64A is about 0.80 inch in length. Distal waist 166 of balloon 110 is bonded by an adhesive bond 168 (such as cyanoacrylate) to spring tip 112 (thereby defining a fourth bonding region 168A), which is in turn attached by weld joint 156 to core 106. The outer diameter of distal waist 166 is about 0.021 inch to 0.029 inch (depending upon balloon outside diameter) and the inner diameter is about 0.016 inch. In fourth bonding region 168A, spring tip 112 has an outer diameter of about 0.014 inch. The diameter of the coil wire which is helically wound to form spring tip 112 is about 0.003 inch.

Spring tip 112 extends about 0.89 inch beyond distal waist 166 of balloon 110. Although not shown in FIG. 7, spring tip 112 is also connected to core 106 proximally of joint 156 by a brazed or soldered bond within fourth bonding region 168A, as illustrated for the similar catheter spring tip structure seen in FIG. 3.

In a preferred embodiment of catheter 100, a vent tube 175 is disposed within balloon 110. Vent tube 175 has a proximal end 177 and a distal end 179. At its distal end 179, vent tube 175 is flattened and secured within epoxy bond material 168 of fourth bonding region 168A. Vent tube 175 extends proximally therefrom through the interior of balloon 110 and has its proximal end 177 secured within epoxy bond 163 of third bonding region 163A between waist tube 108 and proximal waist 162 of balloon 110. At its proximal end 177, vent tube 175 has an outlet 181 which is open to the exterior of catheter 100. Adjacent its distal end 179 and within the interior of balloon 110, vent tube 175 has one or more inlets 183 to facilitate the passage of gases from the interior of balloon 110 into vent tube 175 and to outlet 181. In a preferred embodiment, vent tube 175 has an outer diameter of about 0.003 inch and an inner diameter (vent lumen) of about 0.002 inch, and is made of material such as polyimide.

Prior to use in a patient, catheter 100 is connected to an inflation device (not shown) through luer fitting 114 and inflation fluid (typically, a 50/50 solution of radiopaque dye and saline) is supplied under pressure through the interior of tube 104 and waist tube 108 to the interior of balloon member 110. This fluid pressurizes balloon 110 and purges air contained within the interior of catheter 100 out through inlet 183 of vent tube 175 and through tube 175 to the catheter's exterior via outlet 181. Vent tube 175 and its openings are sized such that fluid pressure can be supplied to inflate balloon 110 without significant leaking of inflation fluid, and so that air and a small plug of fluid will enter vent tube 175. When the air has been purged from the interior of catheter 100, the inflation device is then used to draw the fluid back so as to depressurize catheter 100 and collapse balloon 110 around core 106 (waist tube 108 does not collapse, however, because it is formed from a high strength material). This provides a low profile for balloon 110 while catheter 100 is being inserted into the patient's vascular system. The plug of liquid within vent tube 175, however, blocks air from re-entering the interior of balloon 110.

The advance of inflation fluid into vent tube 175 is controlled by the same factors as discussed above with respect to the advance of contrast liquid into passage 38 in the embodiment illustrated in FIGS. 1 and 2. Again, this applies both during the application of positive pressure and vacuum. Accordingly, catheter 100 is not only ventable through vent 175, but also self-sealing in that no additional seal or valve is required to prevent inflation fluid and pressure from bleeding off vent tube 175.

After purging, catheter 100 is used by inserting it into the patient's vascular system until its distal end is advanced to the location of the stenosis to be treated. The use of a thin-walled metal tube results in significant advantages in steerability, pushability and torqueability characteristics for catheter 100. Thin-walled metal tube 104 provides sufficient flexibility through traverse bends in the vascular system, yet has pushability and torque transmitting characteristics not found in prior art fixed wire catheters. In addition, the use of a hypotube for the relatively long proximal section of the catheter tube provides a tube with a smaller outer diameter, thereby providing enhanced trackability during the angioplasty procedure.

In conclusion, the present invention is an improved angioplasty dilatation balloon catheter of the "non-over-the-wire" type. In other words, it does not require a guide wire which passes through its entire length. With the present invention, a very low shaft diameter can be achieved without sacrificing pushability or torque transfer characteristics.

Although the present invention has been described with reference to preferred embodiments, workers skilled in the art will recognize that changes may be made in form and detail without departing from the spirit and scope of the invention.

What is claimed is:

1. An intravascular balloon catheter, comprising:
   a. a balloon having a proximal waist segment, an inflatable segment and a distal waist segment;
   b. a metallic tube having a proximal end, a distal end and an inflation lumen extending therethrough, the distal end of the metallic tube connected to the proximal waist segment of the balloon, the distal end of the metallic tube having a crimped portion; and
   c. a hollow core member having a proximal end, a distal end and a lumen therein, the proximal end of the hollow core member connected to the distal end of the metallic tube such that the lumen of the hollow core member is in communication with the exterior of the balloon catheter, the distal end of the hollow core member connected to the distal balloon waist.

2. An intravascular balloon catheter, comprising:
   a. a balloon having a proximal waist segment, an inflatable segment and a distal waist segment;
   b. a metallic tube having a proximal end, a distal end and an inflation lumen extending therethrough, the distal end of the metallic tube connected to the proximal waist segment of the balloon; and
   c. a hollow core member having a proximal end, a distal end and a lumen therein, the proximal end of the hollow core member connected to the proximal waist segment such that the lumen of the hollow core member is in communication with the exterior of the balloon catheter, the distal end of the hollow core member connected to the distal balloon waist, the proximal end of the hollow core member partially laterally offset form the distal end of the metallic tube.

3. An intravascular balloon catheter as in claim 1 or 2, wherein the distal end of the metallic tube has a diminishing profile.

4. An intravascular balloon catheter as in claim 1 or 2, wherein the inflatable segment of the balloon has an interior and the hollow core member extends at least partially through the interior of the inflatable segment.

5. An intravascular balloon catheter as in claim 4, wherein the distal end of the metallic tube has a diminishing profile.

6. An intravascular balloon catheter as in claim 1, 2 or 5 wherein the distal waist segment of the balloon has an interior and the hollow core member extends at least partially through the interior of the distal waist segment.

7. An intravascular balloon catheter, comprising:
 a. a balloon having a proximal waist segment, an inflatable segment and a distal waist segment;
 b. a metallic tube having a proximal end, a distal end and an inflation lumen extending therethrough, the distal end of the metallic tube connected to the proximal waist segment of the balloon, the distal end of the metallic tube having a lateral portion removed and a distally facing opening in fluid communication with the inflation lumen; and
 c. a hollow core member having a proximal end and a lumen therein, the proximal end of the hollow core member connected to the proximal waist segment such that the lumen of the hollow core member is in communication with the exterior of the balloon catheter.

8. An intravascular balloon catheter as in claim 1 or 2, wherein the proximal waist segment of the balloon has an interior and the hollow core member extends at least partially through the interior of the proximal waist segment.

9. An intravascular balloon catheter as in claim 1, 2 or 7 wherein the proximal waist segment of the balloon and the inflatable segment of the balloon are integrally formed.

10. An intravascular balloon catheter, comprising:
 a. a hypotube proximal shaft portion having a proximal end and a distal end, the distal end of the hypotube shaft having a crimped portion;
 b. a tubular member having a proximal end, a distal end and a lumen extending therethrough, the proximal end of the tubular member connected to the distal end of the hypotube shaft such that the lumen of the tubular member is in communication with the exterior of the balloon catheter; and
 c. a balloon having a distal end, the distal end of the balloon connected to the distal end of the tubular member.

11. An intravascular balloon catheter, comprising:
 a. a hypotube proximal shaft portion having a proximal end and a distal end;
 b. a balloon having a proximal end and a distal end; and
 c. a tubular member having a proximal end, a distal end and a lumen extending therethrough, the proximal end of the tubular member connected to the proximal end of the balloon such that the lumen of the tubular member is in communication with the exterior of the balloon catheter, the distal end of the tubular member connected to the distal end of the balloon, the proximal end of the tubular member connected to and partially laterally offset form the distal end of the hypotube shaft.

12. An intravascular balloon catheter as in claim 10 or 11, wherein the distal end of the hypotube shaft has a diminishing profile.

13. An intravascular balloon catheter as in claim 10 or 11, wherein the balloon has an interior and the tubular member extends at least partially through the interior.

14. An intravascular balloon catheter as in claim 13, wherein the distal end of the metallic tube has a diminishing profile.

15. An intravascular balloon catheter, comprising:
 a. an inflatable balloon segment;
 b. a metallic tube having a proximal end, a distal end and an inflation lumen extending therethrough, the distal end of the metallic tube having a crimped portion;
 c. a proximal waist having a proximal end, a distal end and a lumen extending therethrough, the proximal end of the proximal waist connected to the distal end of the metallic tube, the distal end of the proximal waist connected to the inflatable balloon segment;
 d. a distal waist having a proximal end and a distal end, the proximal end of the distal waist connected to the inflatable balloon segment; and
 e. a hollow tubular member having a proximal end, a distal end and a lumen therein, the proximal end of the hollow tubular member connected to the distal end of the metallic tube such that the lumen of the hollow tubular member is in communication with the exterior of the balloon catheter, the distal end of the hollow tubular member connected to the distal waist.

16. An intravascular balloon catheter, comprising:
 a. an inflatable balloon segment;
 b. a metallic tube having a proximal end, a distal end and an inflation lumen extending therethrough;
 c. a proximal waist having a proximal end, a distal end and a lumen extending therethrough, the proximal end of the proximal waist connected to the distal end of the metallic tube, the distal end of the proximal waist connected to the inflatable balloon segment;
 d. a distal waist having a proximal end and a distal end, the proximal end of the distal waist connected to the inflatable balloon segment; and
 e. a hollow tubular member having a proximal end, a distal end and a lumen therein, the proximal end of the hollow tubular member connected to the proximal waist such that the lumen of the hollow tubular member is in communication with the exterior of the balloon catheter, the distal end of the hollow tubular member connected to the distal waist, the proximal end of the hollow tubular member partially laterally offset form the distal end of the metallic tube.

17. An intravascular balloon catheter as in claim 15 or 16, wherein the distal end of the metallic tube has a diminishing profile.

18. An intravascular balloon catheter as in claim 15 or 16, wherein the inflatable balloon segment has an interior and the hollow tubular member extends at least partially through the interior of the inflatable segment.

19. An intravascular balloon catheter as in claim 18, wherein the distal end of the metallic tube has a diminishing profile.

20. An intravascular balloon catheter, comprising:
 a. an inflatable balloon segment;
 b. a metallic tube having a proximal end, a distal end and an inflation tureen extending therethrough, the distal end of the metallic tube having a lateral portion removed and a distally facing opening in fluid communication with the inflation lumen;
 c. a proximal waist having a proximal end, a distal end and a lumen extending therethrough, the proximal end of the proximal waist connected to the distal end of the metallic tube, the distal end of the proximal waist connected to the inflatable balloon segment;
 d. a distal waist having a proximal end and a distal end, the proximal end of the distal waist connected to the inflatable balloon segment; and
 e. a hollow tubular member having a proximal end and a lumen therein, the proximal end of the hollow tubular member connected to the proximal waist such that the lumen of the hollow tubular member is in communication with the exterior of the balloon catheter.

21. An intravascular balloon catheter as in claim 15, 16 or 20 wherein the proximal waist has an interior and the hollow tubular member extends at least partially through the interior of the proximal waist.

22. An intravascular balloon catheter as in claim 15, 16 or 20 wherein the proximal waist and the inflatable balloon segment are integrally formed.

23. An intravascular balloon catheter, comprising:
 a. an elongate shaft having a proximal portion and a distal portion, the proximal portion made of a metallic material and the distal portion made of a polymer material, the metallic portion having a crimped distal end;
 b. an inflatable balloon connected to the distal portion of the elongate shaft; and
 c. a hollow tubular member having a proximal end, a distal end and a lumen therein, the proximal end of the hollow tubular member connected to the elongate shaft such that the lumen of the hollow tubular member is in communication with the exterior of the balloon catheter.

24. An intravascular balloon catheter, comprising:
 a. an elongate shaft having a proximal portion and a distal portion, the proximal portion made of a metallic material and the distal portion made of a polymer material;
 b. an inflatable balloon connected to the distal portion of the elongate shaft; and
 c. a hollow tubular member having a proximal end, a distal end and a lumen therein, the proximal end of the hollow tubular member connected to the elongate shaft such that the lumen of the hollow tubular member is in communication with the exterior of the balloon catheter, the proximal end of the hollow tubular member partially laterally offset form the distal end of the metallic portion of the shaft.

25. An intravascular balloon catheter as in claim 23 or 24, wherein the distal end of the hollow tubular member is connected to the inflatable balloon.

26. An intravascular balloon catheter as in claim 23 or 24, wherein the proximal metallic portion of the elongate shaft has a distal end which has a diminishing profile.

27. An intravascular balloon catheter as in claim 23 or 24, wherein the inflatable balloon has an interior and the hollow tubular member extends at least partially through the interior.

28. An intravascular balloon catheter as in claim 27, wherein the proximal metallic portion of the elongate shaft has a distal end which has a diminishing profile.

29. An intravascular balloon catheter, comprising:
 a. a balloon having a proximal end and a distal end;
 b. a hypotube proximal shaft portion having a proximal end and a distal end, the distal end of the hypotube shaft having a lateral portion removed and a distally facing opening in fluid communication with the inflation lumen; and
 c. a tubular member having a proximal end and a lumen extending therethrough, the proximal end of the tubular member connected to the proximal end of the balloon such that the lumen of the tubular member is in communication with the exterior of the balloon catheter.

30. An intravascular balloon catheter, comprising:
 a. an inflatable balloon;
 b. an elongate shaft having a proximal portion and a distal portion, the proximal portion made of a metallic material and the distal portion made of a polymer material, the balloon connected to the distal portion, the distal end of the metallic portion of the shaft having a lateral portion removed and a distally facing opening in fluid communication with the inflation lumen; and
 c. a hollow tubular member having a proximal end, a distal end and a lumen therein, the proximal end of the hollow tubular member connected to the elongate shaft such that the lumen of the hollow tubular member is in communication with the exterior of the balloon catheter.

* * * * *

UNITED STATES PATENT AND TRADEMARK OFFICE
CERTIFICATE OF CORRECTION

PATENT NO. : 5,567,203

DATED : October 22, 1996

INVENTOR(S) : EUTENEUER et al.

It is certified that error appears in the above-identified patent and that said Letters Patent is hereby corrected as shown below:

On the title page, at [75] Inventors, "Richard C. Mattison, Corcoran" should be --Richard C. Mattison, Zimmerman--; Daniel O. Adams, Blaine" should be --Daniel O. Adams, Orono--; Thomas R. Hektner, Minnetonka" should be --Thomas R. Hektner, Medina--; and "Peter T. Keith, Edina" should be --Peter T. Keith, St. Paul--.

Item [56]
On the title page, at References Cited, U.S. PATENT DOCUMENTS, insert --4,943,278   7/1990   Euteneuer et al. ...................604/96--.

At column 2, line 36, "mad" should be --made--.

At column 5, line 5, delete ","; insert --,-- after ")"; at line 66, "other" should be --another--.

Col. 6, line 45, "Lure" should be --luer--; at line 55, delete ","; at line 57, insert --,-- after ")".

At column 7, line 53, delete "." after "balloon".

At column 10, claim 2, line 15, "form" should be --from--.

At column 10, claim 6, line 1, "1, 2 or 5" should be --1 or 2--.

At column 11, claim 8, line 1, "1 or 2" should be --1, 2 or 7--.

At column 11, claim 11, line 13, "form" should be --from--.

UNITED STATES PATENT AND TRADEMARK OFFICE
CERTIFICATE OF CORRECTION

PATENT NO. : 5,567,203

DATED : October 22, 1996

INVENTOR(S) : EUTENEUER et al.

It is certified that error appears in the above-identified patent and that said Letters Patent is hereby corrected as shown below:

At column 12, claim 16, line 20, "form" should be --from--.

At column 12, claim 20, line 4, "tureen" should be --lumen--.

At column 13, claim 24, line 13, "form" should be --from--.

Signed and Sealed this

Tenth Day of August, 1999

Q. TODD DICKINSON

*Attest:*

*Attesting Officer*      *Acting Commissioner of Patents and Trademarks*